(12) United States Patent
Lawson

(10) Patent No.: US 6,423,071 B1
(45) Date of Patent: Jul. 23, 2002

(54) SURGICAL TOOL AND METHOD FOR PASSING PILOT-LINE SUTURES THROUGH SPINAL VERTEBRAE

(76) Inventor: Kevin Jon Lawson, 2662 Edith Ave., Redding, CA (US) 96001

(*) Notice: Subject to any disclaimer, the term of this patent is extended or adjusted under 35 U.S.C. 154(b) by 182 days.

(21) Appl. No.: 09/624,724

(22) Filed: Jul. 25, 2000

(51) Int. Cl.[7] .............................................. A61B 17/90
(52) U.S. Cl. ...................................................... 606/103
(58) Field of Search ............................... 606/1, 53, 86, 606/103; 254/134.3 R, 134.3 FT

(56) References Cited

U.S. PATENT DOCUMENTS

| | | | |
|---|---|---|---|
| 3,858,848 A | * 1/1975 | MacFetrich | 254/134.3 FT |
| 3,979,106 A | * 9/1976 | Jaques | 254/134.3 FT |
| 4,441,497 A | 4/1984 | Paudler | 128/339 |
| 4,557,259 A | * 12/1985 | Wu | |
| 4,643,178 A | * 2/1987 | Nastari et al. | |
| 4,966,143 A | * 10/1990 | Meinershagen | 606/103 |
| 4,985,022 A | 1/1991 | Fearnot et al. | 604/282 |
| 5,092,868 A | * 3/1992 | Mehdian | 604/74 |
| 5,116,340 A | 5/1992 | Songer et al. | 606/103 |
| 5,456,722 A | 10/1995 | McLeod et al. | 623/13 |
| 5,501,688 A | * 3/1996 | Whiteside et al. | 606/103 |
| 5,536,270 A | 7/1996 | Songer et al. | 606/74 |
| 5,772,663 A | * 6/1998 | Whiteside et al. | 606/74 |
| 5,776,115 A | 7/1998 | Antoshikiw et al. | 604/282 |
| 5,935,133 A | 8/1999 | Wagner et al. | 606/103 |

* cited by examiner

*Primary Examiner*—Jeffrey A. Smith
(74) *Attorney, Agent, or Firm*—Robert Charles Hill

(57) ABSTRACT

A method for installing spine-stabilization components comprises directing a long plastic flexible tool through a sublaminar space of a human spine vertebrae inside the spinal canal. Such tool enters the sublaminar space of a particular one of the human spine vertebrae posteriorly from the intervertebral gap with an adjacent vertebrae. It exits the sublaminar space of the particular one of the human spine vertebrae posteriorly from the intervertebral gap with another opposite-side adjacent vertebrae. A suture is threaded through an eye of the tool. The suture is pulled back through the sublaminar space by withdrawing the long plastic flexible tool. The suture is detached from the long plastic flexible tool. A pulled-through part of the suture is attached to a spinal-fixation wire or cable. The suture is then usable as a pilot-line to draw the spinal-fixation wire or cable through the sublaminar space. The spinal-fixation wire or cable is used to anchor a spinal-fixation system.

5 Claims, 1 Drawing Sheet

SURGICAL TOOL AND METHOD FOR PASSING PILOT-LINE SUTURES THROUGH SPINAL VERTEBRAE

BACKGROUND OF THE INVENTION

1. Field of the Invention

The present invention relates to surgical methods and devices to stabilize vertebra, and more particularly to surgical tools for physicians that are used to install spinal rods or longitudinal members and immobilizing cables between vertebrae.

2. Description of Related Art

Degenerative disc disease accounts for more than 100,000 low back spinal fusion procedures in the United States annually, according to Columbia, Colo. hospitals. The intervertebral disc is a pad of cartilage-type material situated between spinal bones. Each disc serves as a connector, spacer, and shock absorber for the spine. A soft, jelly-like center is contained by outer layers of fibrous tissue. Healthy discs help allow normal turning and bending. Trauma or injury to the spine can cause discs to tear, bulge, herniate, and even rupture. This can be quite painful, as the soft center of the disc leaks, putting pressure on the adjacent nerve roots and spinal cord.

A damaged disc can cause nerve dysfunction and debilitating pain in the back, legs and arms. Typical treatments that provide relief and allow patients to function again include back braces, medical treatment, physical therapy and surgery to remove the disc. A conventional surgical solution removes the bad disc and promotes new bone growth in the space to fuse the adjacent vertebrae together.

A few surgical procedures require the passing of loops of heavy 18-gauge wire or cable leader under the spinal lamina without disturbing the nerves or spinal cord. Each thoracic vertebrae in the back, for example, has a central hole (vertebral canal) through which the spinal cord naturally passes. There is a small space in the posterior corner, adjacent to the lamina, where a cable can be safely passed through. But just forward of this is the spinal cord which is very delicate and absolutely cannot tolerate being significantly disturbed. Neurologic injury has been associated with the passage of wires and cables in these locations.

What is needed is a safe way to pass through cables without running any risk of nicking or damaging the spinal cord or other nerves.

Once a cable has been passed, a device can be used to secure the cables, for example, like that described by Robert J. Songer, et al., in U.S. Pat. No. 5,116,340, issued May 26, 1992. Surgical cables looped through spinal vertebrae can be permanently secured by the crimping pliers of Songer.

SUMMARY OF THE INVENTION

An object of the present invention is to provide a surgical tool for the installation of vertebrae-immobilizing cables.

Another object of the present invention is to provide a method for the installation of vertebrae-immobilizing cables.

Briefly, a surgical tool embodiment of the present invention comprises a moderately flexible curved plastic rod with a loop snare at a distal end. The tool is used to pass a size-1 or size-0 suture through the triangular cross-sectional area behind the spinal cord and inside between the ligamentum flavum on both posterior sides. The suture is then, in turn, used as a pilot-line to pull through a much heavier spinal cable or wire. Such tool is supplied sterile and is disposable, and one-millimeter polyethylene material is preferred. Such cable is connected with other cables and rods to immobilize portions of the spine.

A method embodiment of the present invention for installing spine-stabilization components comprises directing a long plastic flexible tool through a sublaminar space of a human spine vertebrae inside the spinal canal. Such tool enters the sublaminar space of a particular one of the human spine vertebrae posteriorly from the intervertebral gap with an adjacent vertebrae. It exits the sublaminar space of the particular one of the human spine vertebrae posteriorly from the intervertebral gap with another opposite-side adjacent vertebrae. A suture is threaded through an eye of the tool. The suture is pulled back through the sublaminar space by withdrawing the long plastic flexible tool. The suture is detached from the long plastic flexible tool. A pulled-through part of the suture is attached to a spinal-fixation wire or cable. The suture is then usable as a pilot-line to draw the spinal-fixation wire or cable safely through the sublaminar space. The spinal-fixation wire or cable is used to anchor a spinal-fixation system.

An advantage of the present invention is that a surgical tool is provided that simplifies the installation of surgical cables in the spine.

Another advantage of the present invention is that a method is provided that makes it safer to install cables and rods to immobilize damaged portions of the spine.

The above and still further objects, features, and advantages of the present invention will become apparent upon consideration of the following detailed description of specific embodiments thereof, especially when taken in conjunction with the accompanying drawings.

DETAILED DESCRIPTION OF THE INVENTION

Figure 1:
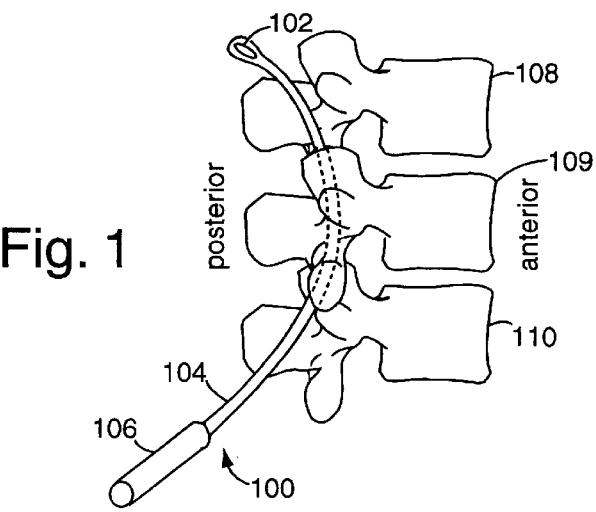
FIG. 1 is a diagram representing the spine of a patient having a spinal implant embodiment of the present invention placed by a surgeon.

FIG. 1 illustrates a surgical tool embodiment of the present invention, and is referred to herein by the general reference numeral 100. The surgical tool 100 is molded from plastic, and includes a snare 102 at the distal end of a flexible rod 104. A handle 106 allows a surgeon to navigate the snare 102 and rod 104 through the spinal canal of a particular spinal vertebrae in a patient during surgery.

A series of vertebrae 108–110 representing a portion of a patient's spine is also illustrated in FIG. 1. The view is from the right side and shows the surgical tool 100 after having been passed through the most posterior corner of the spinal canal of vertebrae 109. The distal end reemerges so a pilot-line can be attached and pulled back through the spinal canal.

A slight curve in the rod 104 assists the surgeon in entering the inferior vertebral notch between left and right ligamentum flavum posterior to the spinal cord. A moderate stiffness in the rod 104 allows the snare 102 to be directed under the lamina and out the superior vertebral notch.

How much stiffness is appropriate is a matter of expert judgment. In one embodiment of the present invention, the whole of surgical tool 100 was injection-molded of polyethylene, the rod 104 was one-millimeter in diameter, and the snare was about 1.5 millimeters. Such also allowed the surgical tool 100 to be supplied sterile and inexpensive enough to be readily disposable. Other resilient materials with such properties can also be used.

Figure 2:
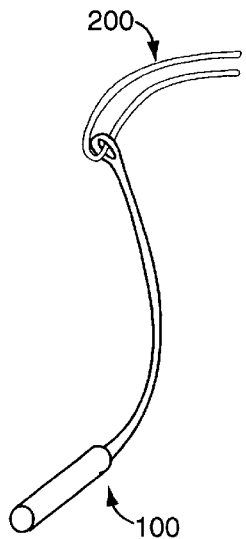
FIG. 2 is an end view over a side view of a stabilization implant embodiment of the present invention similar to that shown in FIG. 1.

Once the snare 102 appears at the superior vertebral notch, a size-0 or size-1 suture can be threaded in the eye. FIG. 2 illustrates a suture 200 after being passed through the eye of the tool.

Referring again to FIG. 1, a surgical tool 100 is then pulled back down with the suture 200 in-tow until it emerges from the inferior vertebral notch. The suture 200 is disconnected from the surgical tool 100 and tied to a heavy surgical cable or wire, e.g., 18-gauge implant-grade stainless steel. The suture is then pulled up like a pilot line to draw the surgical cable through the spinal canal in a precisely controllable maneuver. These cables and wires are then used to secure various spinal fixation rods and plates, e.g., Songer cable systems and ISOLA spinal systems as commercially marketed by AcroMed Corporation (subsidiary of Johnson and Johnson).

Figure 3:
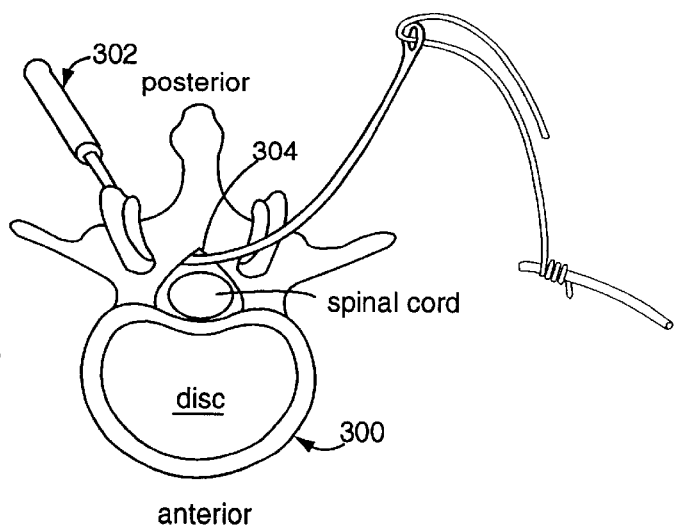
FIG. 3 is a drawing of a tool embodiment of the present invention for placing spinal implant devices in patients during operations.

FIG. 3 shows a spinal thoracic or lumbar vertebrae 300 in a top view. A surgical tool 302, similar to tool 100, is passed through a posterior corner 304 inside the spinal canal and dorsal to the spinal cord. This small triangular-shaped area is flanked by the ligamentum flavum and is a relatively safe for passing through spinal-fixation wires and cables. Such is true for the cervical spine in appropriate circumstances, in addition to the L1–L5 lumbar vertebrae and T1–T12 thoracic vertebrae.

Although particular embodiments of the present invention have been described and illustrated, such is not intended to limit the invention. Modifications and changes will no doubt become apparent to those skilled in the art, and it is intended that the invention only be limited by the scope of the appended claims.

What is claimed is:

1. A spine-stabilization surgical tool, comprising:

a curved rod with a small enough diameter and long enough length to be passed through a sublaminar space of a human spine vertebrae inside the spinal canal;

a loop disposed at a distal end of the rod and able to pass through said sublaminar space without damage to the spinal cord, and for providing a way to draw back a suture through said sublaminar space; and a handle disposed at a near end of the rod and providing for the steerage and penetration pressure necessary for a surgeon to direct the loop through said sublaminar space of a single one of said human spine vertebrae;

wherein, the rod has a stiffness suitable for the handle to push the loop through said sublaminar space of a human spine vertebrae inside the spinal canal, and said suture is used as a pilot-line to draw through a cable or wire in a spinal fixation system.

2. The spine-stabilization surgical tool of claim 1, wherein:

the rod comprises polyethylene and is about one millimeter in diameter.

3. The spine-stabilization surgical tool of claim 1, wherein:

the loop comprises polyethylene and is about one-and-half millimeters in diameter.

4. The spine-stabilization surgical tool of claim 1, wherein:

the rod, loop, and handle are all molded from a single piece of polyethylene.

5. A method for installing spine-stabilization components, the method comprising the steps of:

directing a long plastic flexible tool through a sublaminar space of a human spine vertebrae inside the spinal canal;

entering said sublaminar space of a particular one of said human spine vertebrae posteriorly from the intervertebral gap with an adjacent vertebrae;

exiting said sublaminar space of said particular one of said human spine vertebrae posteriorly from the intervertebral gap with another opposite-side adjacent vertebrae;

threading a suture through an eye of said tool;

pulling said suture back through said sublaminar space by withdrawing said long plastic flexible tool;

detaching said suture from said long plastic flexible tool;

attaching a pulled-through part of said suture to a spinal-fixation wire or cable; and using said suture as a pilot-line to draw said spinal-fixation wire or cable through said sublaminar space;

wherein, said spinal-fixation wire or cable is used to anchor a spinal-fixation system.

\* \* \* \* \*